United States Patent [19]

Noble, deceased et al.

[11] 3,984,915

[45] Oct. 12, 1976

[54] ORTHODONTICS BY MAGNETICS

[76] Inventors: Terry Gordon Noble, deceased, late of San Antonio, Tex.; by Mary Lynne Noble, administratrix, 3223 Old Blue Ridge, San Antonio, Tex. 78230

[22] Filed: June 27, 1975

[21] Appl. No.: 590,934

[52] U.S. Cl. ............................ 32/14 R; 32/DIG. 6
[51] Int. Cl.$^2$ ......................................... A61C 7/00
[58] Field of Search ............ 32/DIG. 6, 14 A, 14 R, 32/1

[56] References Cited
UNITED STATES PATENTS

| | | | |
|---|---|---|---|
| 2,543,773 | 3/1951 | Goldschmidt | 32/DIG. 6 |
| 2,709,301 | 5/1955 | Goldsmith | 32/DIG. 6 |
| 2,803,879 | 8/1957 | Gook | 32/DIG. 6 |

*Primary Examiner*—Jack Q. Lever
*Attorney, Agent, or Firm*—Cox, Smith, Smith, Hale & Guenther Incorporated

[57] ABSTRACT

This invention involves the orthodontic movement of live teeth in the mouth by using the forces of magnets. A magnet is attached to the teeth by conventional methods such as adhesive bonding or dental appliances. The magnets are placed on the teeth in such a manner to employ the attraction and repulsion characteristics of a magnetic field. These forces may be employed to align teeth, tilt teeth, move root positions and angulations, torque teeth, and erupt impacted or partially impacted teeth into the correct position in the mouth. The technique may be used alone or in combination with other conventional orthodontic techniques for either major or minor tooth movement. The magnets may be attached anywhere on a tooth, but preferably in an inconspicuous position. The magnets themselves may have tapered edges to insure the teeth move to the proper position. In the movement of a single tooth normally a magnet will be attached to the single tooth with the other magnet which creates the repulsion or attraction force being attached to several teeth in combination.

8 Claims, 17 Drawing Figures

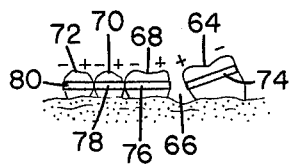
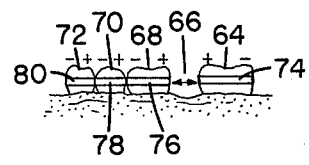
FIG. 5　　　　　　　　FIG. 6
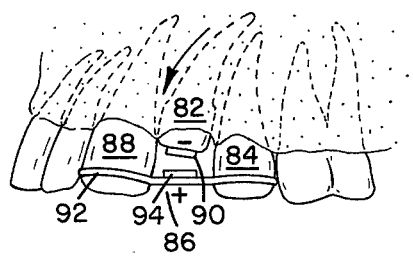
FIG. 7
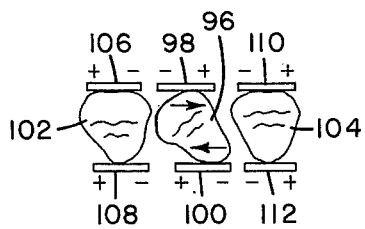
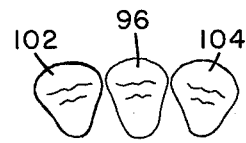
FIG. 8　　　　　　　　FIG. 9
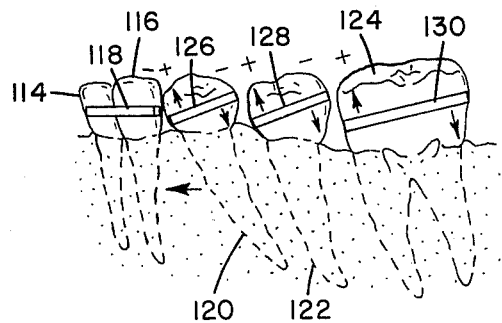
FIG. 10

ORTHODONTICS BY MAGNETICS

BACKGROUND OF THE INVENTION

This invention relates to the orthodontic movement of teeth in the mouth and, more particularly, the orthodontic movement of the teeth using magnets placed on the teeth to attract or repel adjacent magnets. The magnetic forces will be used to move the teeth in the mouth so that the teeth can be properly aligned with the curvature of the mouth.

BRIEF DESCRIPTION OF THE PRIOR ART

Prior to the present invention, the conventional way for moving live teeth in the mouth by an orthodontist usually involved the attachment of dental appliances (such as braces) so that a constant force was exerted on the tooth that needed to be moved. An elastic member creating the constant force would continually have to be tightened or strengthened by repeated adjustments by a dentist or orthodontist. Many times dental appliances such as a retainer wire would be required across the front of the teeth to prevent excessive movement of the teeth. Depending upon the type of movement that is desired individual, wire braces or other types of removable dental appliances may be necessary; however, all the methods presently employed by dentists and orthodontists in the movement of teeth require repeated adjustments to insure the proper movement, not to mention the inconvenience and unsightly appearance of the removable dental appliances.

Fairly recently a direct bonding technique was developed wherein many of the dental appliances that were formerly attached to the teeth by wire structures are now being attached by a direct bond. One type of direct bonding technique uses an acid to etch the surface of the teeth. Next an adhesive compound is applied to the etched area. The adhesive compound hardens very rapidly to hold the dental appliance to the teeth. While this method of direct bonding has been successful for limited use, it has still not met with widespread acceptance by the dental profession.

Also prior to the present invention many types of magnetic forces have been used in combination with dentures and the retaining of dentures in the mouth. A typical such example is U.S. Pat. No. 3,798,770, a copy of which is attached herewith. Normally for the retaining of dentures in position, either magnets are located in the gum with an opposite and attracting magnet being located in the denture, or like magnets for repulsion are located in the upper and lower denture. Magnets have also been used to locate dentures in the proper position in the mouth or to hold side by side dentures in the correct position. However, none of the methods employing magnets have used the magnets to move live teeth in the mouth as would normally require extensive treatment by an orthodontist.

SUMMARY OF THE INVENTION

It is an object of the present invention to move live teeth in the mouth to the proper locations along the curvature of the mouth.

It is another object of the present invention to employ magnetics in the movement of teeth wherein magnetic forces either repel or attract magnets attached to adjacent teeth and/or structure.

It is an object of the present invention to employ the use of magnets attached to adjacent teeth for the opening or closure of spaces for the proper alignment of the teeth.

It is yet another object of the present invention to attach magnets to teeth by direct bonding with the forces of magnets attached to the teeth being used to correctly align the teeth with the curvature of the mouth.

It is still another object of the present invention to provide a continuing force on misaligned teeth to move the teeth to the correct position thereby creating the proper bite of the teeth, proper spacing, and proper curvature of the mouth.

It is even another object of the present invention to employ the use of magnetics in conjunction with conventional orthodontic techniques to move teeth in the mouth wherein the number of adjustments will be greatly reduced thereby reducing the total cost of the dental work.

BRIEF DESCRIPTION OF THE DRAWINGS

FIG. 5 is a perspective view of representative teeth having spacing problems.

FIG. 6 is a perspective view of the teeth as shown in FIG. 5 after employing magnetics to correct the spacing problem.

FIG. 7 is a perspective view of an impacted tooth and the use of magnetics to properly align the impacted tooth.

FIG. 8 is a top view of twisted teeth showing how magnets can be attached thereto.

FIG. 9 is a top view of the teeth as shown in FIG. 8 after the twisted tooth has been torqued by magnetic forces to the proper position.

FIG. 10 is a perspective view of teeth with crooked roots showing how magnets may be attached thereto.

DESCRIPTION OF THE PREFERRED EMBODIMENT

Figure 1:
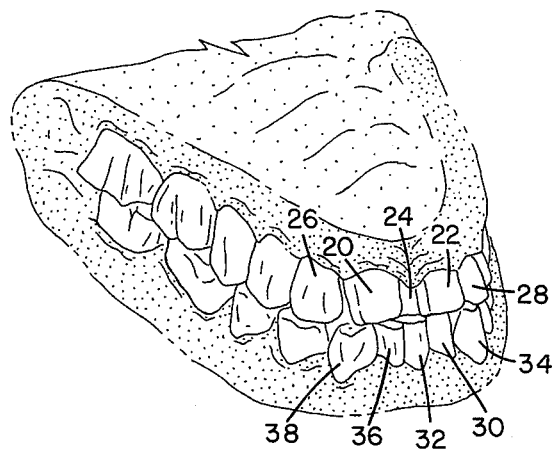
FIG. 1 is a perspective view of an individual's teeth that have spacing problems.
Figure 2A:
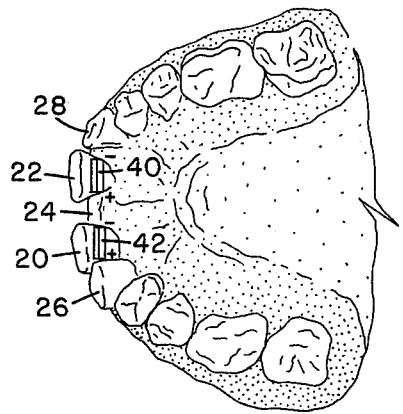
FIG. 2a is a bottom view of the upper teeth shown in FIG. 1.
Figure 2B:
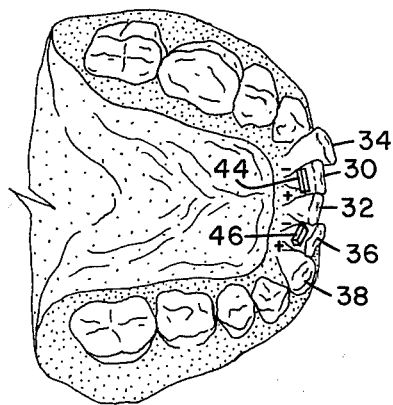
FIG. 2b is a top view of the lower teeth shown in FIG. 1.

Referring now to FIGS. 1, 2a and 2b in combination, there is illustrated a typical set of teeth having problems that can be corrected by the use of magnetics.

While FIG. 1 may appear to be a set of dentures, it is in fact a pictorial perspective view of the live teeth of an individual. Between the incisors 20 and 22 is located a space 24. In proper dental practice it would be advisable to move the incisors 20 and 22 together to close the space 24. After moving the incisors 20 and 22 together to occupy the space 24 the adjacent teeth 26 and 28 may also have to be moved to further close other smaller spaces created to give a uniform appearance; however, if the space 24 is closed by realignment of teeth 20, 22, 26 and 28 the lower teeth which are already overcrowded would not allow a proper overbite. The lower teeth which are overcrowded can be correctly positioned by removing either incisors 30 or 32, preferably incisors 32. After incisor 32 has been removed the front teeth, represented by incisor 30, tooth 34, tooth 36 and tooth 38, may be repositioned in the mouth to fill the gap vacated by incisor 32. This would also allow additional room for the closing of space 24 between incisors 20 and 22.

Referring now to FIG. 2a magnets may be attached to incisors 20 and 22 by any conventional means such as dental appliances; however, in the preferred embodiment a magnet 40 is directly bonded to the linqual side of incisor 22. The direct bonding technique as has been recently developed normally uses an acid to etch the surface prior to the bonding to the tooth by an adhesive compound. The magnet 40 extends across the tooth as depicted in the drawing with one end of the magnetised bar being pointed toward incisor 20. Also on the lingual side of incisor 20 is attached a magnet 42 by any conventional means such as direct bonding. Because the space 24 is to be filled, magnets 40 and 42 should be arranged so that opposite poles are adjacent each other for an attraction of magnetic forces. As shown in FIG. 2a, magnet 40 has a positive pole that is attracting the negative pole of magnet 42; however, both magnets may have a reverse polarity.

Once incisors 20 and 22 have come together they will be physically held together by dental appliances and/or magnets. Magnets will then be placed on adjacent teeth 26 and 28 for attraction to the magnets still remaining on incisors 20 and 22. Though it may be necessary to move additional teeth, probably the movement of the four front teeth 20, 22, 26 and 28 will be sufficient for closing the space 24. After the space 24 has been closed, and all upper teeth are in their proper position, the magnets may be removed by any conventional means such as the grinding off the magnet and adhesive bonding compound.

Concerning the lower teeth as shown in FIG. 2b incisor 32 will be pulled and magnets 44 and 46 attached to incisor 30 and tooth 36, respectively. Opposite poles of magnets 44 and 46 will be located adjacent to each other so that incisor 30 and tooth 36 will move together filling the space vacated by the removal of incisor 32. After teeth 30 and 36 have filled the space created by the removal of incisor 32, they will be held together by the magnets or dental appliances. Next, magnets will be attached to teeth 34 and 38 to pull them into the space created upon movement of teeth 30 and 36. Notice in particular that tooth 34 will be pulled inward as well as toward the center of the mouth thereby eliminating the unsightly protrusion of tooth 34. Once all of the teeth have been moved that are necessary for the closure of the space created by the removal of tooth 32, and to eliminate unsightly protrusions, there should be enough room for the overbite of the corrected upper teeth previously shown as FIG. 2a. It should be understood that the moving of the upper teeth and lower teeth would take place simultaneously with magnetics being applied to both the upper set and lower set.

While the moving of the teeth as shown in FIGS. 1, 2a and 2b have been described in conjunction with magnets adhesively bonded to the teeth, it should be understood that dental appliances such as bands around the teeth with a means for holding a magnet into position may be used without departing from the principle of the invention. If the normal dental or orthodontic practices were followed, a tension created by a dental appliance would have to pull the teeth into position by a gradual pulling force. As the teeth would move the tension device would have to be continually adjusted requiring repeated trips to the doctor at a substantial expense to the patient. By the use of magnetics, fewer adjustments are required, not to mention a lower cost of initial installation.

Figure 3:
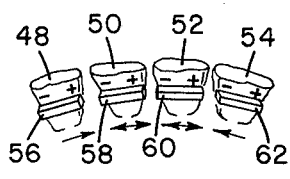
FIG. 3 is a perspective view of teeth having spacing problems.
Figure 4:
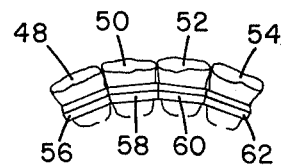
FIG. 4 is a perspective view of the teeth shown in FIG. 3 after employing magnetics to eliminate spacing problems.

Referring now to FIG. 3 of the drawings there is shown a series of teeth 48, 50, 52 and 54 having spaces therebetween. The space between the teeth 48, 50, 52 and 54 may be closed by the use of magnets 56, 58, 60 and 62 attached to each tooth, respectively. While the magnets may be attached by any conventional means the preferred method of attachment is by direct bonding with opposite poles of each magnet being adjacent to each other for magnetic attraction. FIG. 4 shows the teeth 48, 50, 52 and 54 in their closed position after the magnets 56, 58, 60 and 62 have moved each respective tooth to its new position.

Some times when a tooth is missing, or there is an unusual aount of space between teeth, one tooth will gradually move into the vacant space. It may be necessary to move a tooth back to its normal position or a new position so that a bridge may be inserted in the space. Referring to FIG. 5, molar 64 has migrated into a space 66 over a period of time. The space 66 should be filled with a bridge, however, space 66 is not large enough for a normal bridge. While molar 64 may be moved by magnetic forces, if a single magnet were placed on molar 64 and adjacent tooth 68, the adjacent tooth 68 may be moved out of alignment. However, if adjacent tooth 68 is clamped together with tooth 70 and 72 by a normal dental appliance such as a band, repulsion magnets could be used to move molar 64. On molar 64 a magnet 74 is attached thereto by direct bonding. The magnet 76 that is located on tooth 68 repels the magnet 74 located on tooth 64. Rather than using a dental appliance to clamp teeth 68, 70 and 72 together, attraction magnets may be used wherein the magnet 76 on tooth 68 attracts magnet 78 on tooth 70, and likewise magnet 78 attracts magnet 70 on tooth 72. By the use of the magnetic forces, tooth 64 will be moved to the position as shown in FIG. 6 so that space 66 has been enlarged to allow a bridge to be inserted therein.

It is quite common for a tooth to become impacted in the gum below other teeth even though a space is available where the tooth should be. Referring to FIG. 7, an impacted tooth 82 is located above the curvature of the mouth. Space 86 between tooth 84 and 88 is available wherein the impacted tooth 82 should be located. To move the tooth 82 into its correct position, if necessary the gum is opened and a magnet 90 is attached to the impacted tooth 82. An appliance 92 is connected to tooth 82 and 88 for holding magnet 94 into position over the impacted tooth 82. The magnet 94 attracts the magnet 90 thereby causing the impacted tooth 82 to move into the space 86. Once the impacted tooth 82 is in its correct position the magnets 90 and 94 and the appliance 92 are removed.

Many times a tooth may be twisted in the mouth thereby requiring a torque be applied thereto to relocate the tooth in its proper position. Referring now to FIG. 8, tooth 96, which is shown in a top view, is twisted out of its normal position. By the attachment of the proper magnets 98 and 100 on each side of tooth 96 for attraction or repulsion from magnets located on teeth 102 and 104, the tooth 96 may be torqued back into its normal position. On tooth 102 magnet 106 repels magnet 98 and magnet 108 attracts magnet 100. Likewise, on tooth 104 magnet 110 attracts magnet 98 and magnet 112 repels magnet 100. After the torquing of tooth 96, the teeth will reach the position as shown in FIG. 9.

Sometimes a tooth will grow at an angle and the roots will need to be brought into alignment or an upright position. Referring to FIG. 10, teeth 114 and 116 which are in the proper position are connected together with a magnet 118 being attached thereto. Teeth 120, 122 and 124, each of which have crooked roots also have magnets 126, 128 and 130 connected thereto, respectively. By use of attraction of magnetic forces the gradual force as exerted by the magnets pictorially illustrated in FIG. 10 will swing the roots of teeth 120, 122 and 124 into the proper position.

Figure 11:
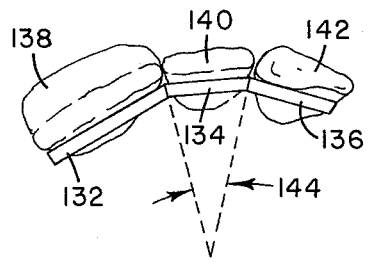
FIG. 11 is a top view of teeth having magnets attached thereto with the ends of the magnets being cut to aid in the alignment of the teeth.

By the cutting of angles on each end of the magnets, as the magnets are brought together a torquing force can be applied to the tooth against which the magnet is attached. Referring for example to FIG. 11, magnets 132, 134 and 136 are attached to teeth 138, 140 and 142, respectively. When each end of the magnets 132, 134 and 136 are brought into an abutting relationship an angle 144 is created by the projection of the planes between the magnets. The force created by the end surfaces of the magnets tend to torque the teeth into the proper position upon closure of open spaces between the teeth. To determine the proper position of the teeth and the planes for the ends of the magnets, it is normal in dental work for a stone model of the teeth to be made by the dentist. The teeth on the stone model are then cut off and arranged in the proper position as desired by the dentist or orthodontist with the magnets being attached to the teeth of the model. Next the dentist can go back to the patient and then arrange the magnets on the teeth to move the teeth to the desired position as previously calculated in the laboratory. since the magnets tend to come into flush contact, angulation of the roots can be corrected by using the proper cut on each magnet.

Figure 12:
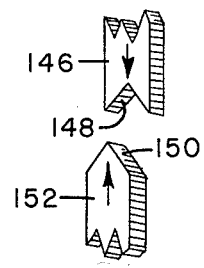
FIG. 12 is a perspective view of opposing magnets that may be used for angle and torque forces on the teeth.

If opposing magnets are used between upper and lower teeth it may be possible to use a sloping or notched surface to apply angle and torque force between the teeth. For example, in FIG. 12 the upper magnet 146 has a notch 148 cut therein that is offset from the wedge 150 cut in the mating end of lower magnet 152. As the upper magnet 146 and lower magnet 152 come together the notch 148 in wedge 150 apply an angular and torque force on the teeth attached thereto.

Figure 13:
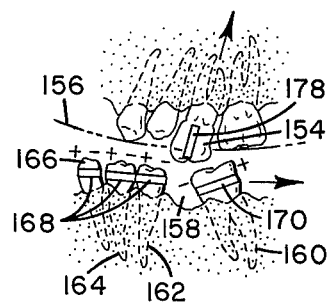
FIG. 13 is a perspective view of magnets being used to open the space between teeth and depress an over-erupted tooth.

It is quite common for a tooth that does not have a mating tooth on the opposite side of the mouth to become erupted and extend beyond the normal curvature of the mouth. To restore the curvature of the mouth, it is necessary to depress the erupted tooth back into its normal position by the applying of a constant force. Referring now to FIG. 13 an erupted tooth 154 extends beyond the normal curvature of the mouth represented by line 156. Also because of the space 158, the adjacent teeth have migrated towards the space 158. Tooth 160 should be moved to the right and teeth 162, 164 and 166 should be moved to the left. By the attachment of magnets 168 to teeth 162, 164 and 166 that repel magnet 170 attached to tooth 160, space 158 can be reopened. Likewise, by having a repelling magnet in erupted tooth 154 it will be depressed into its normal position.

Figure 14:
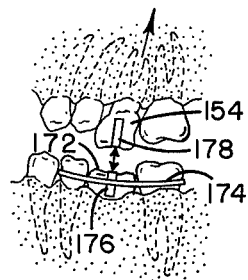
FIG. 14 is a perspective view of magnets being used on teeth to depress an over-erupted tooth.

If the space 158, as described in FIG. 13, has not been filled by the adjacent teeth a bridge 172 may be inserted therein as shown in FIG. 14. The bridge 172 which will be attached to the adjacent teeth by an appliance 174 also has a magnet 176 attached thereto. By locating a repelling magnet 178 on erupted tooth 154, the erupted tooth 154 can be depressed back into its normal position. It should be understood that the bridge 172 must initially allow the tooth 154 to protrude, and as the tooth 154 is depressed, the bridge 174 may be replaced by a larger bridge to reestablish the curvature of the mouth.

While numerous methods of using magnetic forces to move teeth have been described in the present patent application, it should be realized that there are many other possible ways that a person's live teeth may be moved by the use of magnetic forces even though not specifically described herein and still not deviate from the scope and intent of the present invention.

Figure 15:
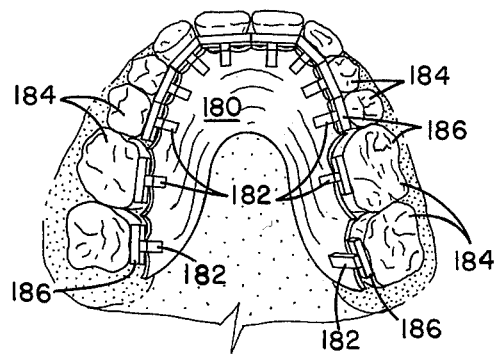
FIG. 15 is a top view of a tooth having a retainer with magnets thereon to hold the tooth in position.

In most uses, after the teeth have been moved, the roots do not become securely located for a period of time. Therefore, it may be necessary for a retainer to hold the teeth in position while the roots are becoming set. FIG. 15 is an example wherein a retainer 180 has a series of magnets 182 located thereon. Likewise the teeth 184 have magnets 186 located on the lingual side. since each magnet 182 on the retainer 180 attracts a magnet 186 on the teeth 184, the teeth will be securely held into position. It may be possible for the magnets 186 to abutt each other and retain the teeth in position, but it would depend on the individual case.

Figure 16:
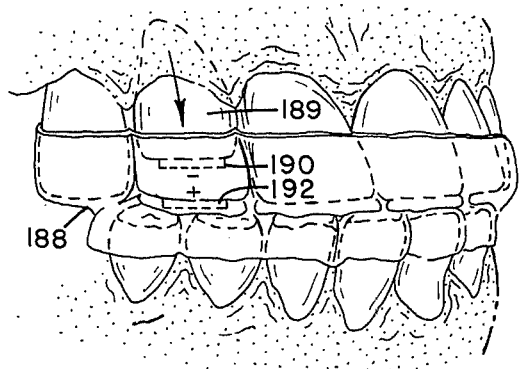
FIG. 16 is an elevated view of teeth with a bite plate therebetween and having magnets to move an impacted tooth.

In FIG. 16 a biting plate 188 is used by the patient during periods when the mouth will not be in use. It is quite common for the patient to sleep with a biting plate to hold teeth in position. If the patient has an impacted tooth 189, a magnet 190 attached to the tooth 189 can attract a magnet 192 attached to the biting plate 181 to move the impacted tooth 189 into its proper position.

We claim:

1. A method for moving teeth in a patient's mouth comprising the steps of:
examining the patient to determine if teeth need to be moved;
attaching at least two magnets in the patient's mouth with at least one of said magnets being attached to a tooth that needs to be moved, said magnets exerting magnetic forces on each other to gradually move said tooth;
adjusting said magnets as necessary for proper movement of said tooth; and
removing said magnets from said teeth.

2. The method for moving teeth as recited in claim 1 including the step of relocating magnets on said teeth to move additional teeth after the tooth being moved has been properly located.

3. The method for moving teeth as recited in claim 1 wherein several teeth are being moved simultaneously to establish a proper curvature of the mouth.

4. The method for moving teeth as recited in claim 1 wherein said attaching includes:
   etching an area of the teeth with acid;
   applying an adhesive substance to said area; and
   mounting said magnets with said adhesive substance.

5. The method for moving teeth as recited in claim 4 wherein said removing includes the grinding of said adhesive substance and said magnets off said teeth.

6. The method for moving teeth as recited in claim 1 including after said examining step the step of cutting planar surfaces on ends of said magnets to torque teeth upon abutting of said magnets.

7. The method of moving teeth as recited in claim 6 further including after the examining step the step of diagraming planned movement of said teeth.

8. The method for moving teeth as recited in claim 1 wherein said attaching step includes connecting dental appliances to said teeth for holding said magnets to said teeth.

* * * * *